(12) United States Patent
Rosen

(10) Patent No.: US 9,675,582 B2
(45) Date of Patent: Jun. 13, 2017

(54) ALTERNATIVE ACT WITH NATURAL BOTANICAL ACTIVE GRAS INGREDIENTS FOR TREATMENT AND PREVENTION OF THE ZIKA VIRUS

(71) Applicant: U.S. Phytotherapy, Inc., Oviedo, FL (US)

(72) Inventor: Bob D. Rosen, Oviedo, FL (US)

(73) Assignee: U.S. Phytotherapy, Inc., Oviedo, FL (US)

( * ) Notice: Subject to any disclaimer, the term of this patent is extended or adjusted under 35 U.S.C. 154(b) by 0 days.

(21) Appl. No.: 15/148,522

(22) Filed: May 6, 2016

(65) Prior Publication Data
US 2016/0250181 A1 Sep. 1, 2016

Related U.S. Application Data

(60) Continuation-in-part of application No. 14/933,229, filed on Nov. 5, 2015, now Pat. No. 9,358,261, which
(Continued)

(51) Int. Cl.
*A61K 31/165* (2006.01)
*A23L 33/105* (2016.01)
(Continued)

(52) U.S. Cl.
CPC .......... *A61K 31/366* (2013.01); *A23L 33/105* (2016.08); *A61K 9/2018* (2013.01);
(Continued)

(58) Field of Classification Search
CPC .............. A61K 2300/00; A61K 31/165; A61K 31/357; A61K 31/365; A61K 31/366;
(Continued)

(56) References Cited

U.S. PATENT DOCUMENTS 4,749,708 A 6/1988 Maroko
4,761,417 A 8/1988 Maroko
(Continued)

FOREIGN PATENT DOCUMENTS

EP 2289554 3/2011
JP 2009051803 3/2009

OTHER PUBLICATIONS

Wormwood [online] retrieved on Jan. 25, 2017 from: http://www.botanical.com/botanical/mgmh/w/wormwo37.html; 8 pages.*
(Continued)

*Primary Examiner* — Ernst V Arnold
(74) *Attorney, Agent, or Firm* — Brian S. Steinberger; Law Offices of Brian S. Steinberger, P.A.

(57) ABSTRACT

An all-natural active ingredient herbal compositions and methods of preparing the same are provided. The novel Artemisinin Combination Therapy (ACT) consists of artemisinin, derivatives of artemisinin, berberine, capsaicin and *Tinospora Cordifolia*. When formulated in a gel cap, the composition can consist of only artemisinin, berberine, capsaicin, and *Tinospora cordifolia*. A blended mixture and inert ingredients, such as selected excipient compounds, are mixed together with artemisinin, berberine, capsaicin, and *Tinospora cordifolia* and compressed to form a single pill, tablet, or capsule for the treatment of Zika virus. A tablet or pill for children is formulated to be chewable.

15 Claims, 3 Drawing Sheets

Related U.S. Application Data is a continuation-in-part of application No. 14/614,946, filed on Feb. 5, 2015, now Pat. No. 9,186,331, which is a division of application No. 13/660,553, filed on Oct. 25, 2012, now Pat. No. 9,011,892.

(60) Provisional application No. 61/550,969, filed on Oct. 25, 2011, provisional application No. 62/306,973, filed on Mar. 11, 2016.

(51) Int. Cl.

| | | |
|---|---|---|
| *A61K 31/366* | (2006.01) | |
| *A61K 31/4741* | (2006.01) | |
| *A61K 36/59* | (2006.01) | |
| *A61K 45/06* | (2006.01) | |
| *A61K 9/20* | (2006.01) | |
| *A61K 31/365* | (2006.01) | |
| *A61K 31/4375* | (2006.01) | |
| *A61K 31/4745* | (2006.01) | |
| *A61K 31/357* | (2006.01) | |

(52) U.S. Cl.
CPC .......... *A61K 31/165* (2013.01); *A61K 31/357* (2013.01); *A61K 31/365* (2013.01); *A61K 31/4375* (2013.01); *A61K 31/4741* (2013.01); *A61K 31/4745* (2013.01); *A61K 36/59* (2013.01); *A61K 45/06* (2013.01)

(58) Field of Classification Search
CPC ............ A61K 31/4375; A61K 31/4741; A61K 31/4745; A61K 36/59; A61K 45/06; A61K 9/2018; A23L 33/105
See application file for complete search history.

(56) References Cited

U.S. PATENT DOCUMENTS

| | | | |
|---|---|---|---|
| 4,980,344 | A | 12/1990 | Maroko |
| 5,153,178 | A | 10/1992 | Maroko |
| 5,225,427 | A | 7/1993 | Venugopalan |
| 5,225,562 | A | 7/1993 | McChesney |
| 5,413,928 | A | 5/1995 | Weathers |
| 5,856,351 | A | 1/1999 | Zheng |
| 6,127,405 | A | 10/2000 | Kumar |
| 6,136,847 | A | 10/2000 | Posner |
| 6,160,004 | A | 12/2000 | Posner |
| 6,306,896 | B1 | 10/2001 | Scheiwe |
| 6,346,631 | B1 | 2/2002 | Jain |
| 6,461,603 | B2 | 10/2002 | Bentley |
| RE38,117 | E | 5/2003 | Zheng |
| 6,610,327 | B1 | 8/2003 | Bosche |
| 6,649,647 | B1 | 11/2003 | Haynes |
| 6,683,193 | B2 | 1/2004 | Bhakuni |
| 6,685,972 | B2 | 2/2004 | Kumar |
| 6,737,438 | B2 | 5/2004 | Singh |
| 6,750,356 | B1 | 6/2004 | Bhakuni |
| 6,906,098 | B2 | 6/2005 | Solaja |
| 6,906,205 | B2 | 6/2005 | Vennerstrom |
| 6,984,640 | B1 | 1/2006 | Haynes |
| 7,071,226 | B1 | 7/2006 | Singh |
| 7,098,242 | B2 | 8/2006 | ElSohly |
| 7,482,334 | B2 | 1/2009 | Frincke |
| 7,547,687 | B2 | 6/2009 | Reading |
| 7,915,223 | B2 | 3/2011 | Mor |
| 7,935,839 | B2 | 5/2011 | Frincke |
| 7,947,846 | B2 | 5/2011 | Frincke |
| 8,026,209 | B2 | 9/2011 | Gaillard |
| 9,011,892 | B2 | 4/2015 | Rosen et al. |
| 9,186,331 | B2 | 11/2015 | Rosen et al. |
| 2005/0148628 | A1 | 7/2005 | Muller |
| 2006/0233895 | A1 | 10/2006 | Brown |
| 2009/0098207 | A1 | 4/2009 | Malakhov |
| 2011/0206636 | A1 | 8/2011 | Sas |
| 2013/0072513 | A1 | 3/2013 | Colman |

OTHER PUBLICATIONS

Cloves [online] retrieved on Jan. 25, 2017 from: http://www.newworldencyclopedia.org/entry/Clove; 6 pages.*
CDC Zika Virus Prevention [online] retrieved on Jan. 25, 2017 from: https://www.cdc.gov/zika/prevention/; 2 pages).*
Goswami, et al., Anti-Helicobacter pylori Potential of Artemisinin and Its Derivatives, Antimicrobial Agents and Chemotherapy, 2012, pp. 4594-4607, vol. 56, No. 9.
Lee, et al., Berberine ameliorates TNBS-induced colitis by inhibiting lipid peroxidation, enterobacterial growth and NF-kB activation, European Journal of Pharmacology, 2010, pp. 162-170, vol. 648.
Li, et al., Berberine inhibits acute radiation intestinal syndrome in human with abdomen radiotherapy, Med Oncol, 2010, pp. 919-925, vol. 27.
Yan, et al., Berberine promotes recovery of colitis and inhibits inflammatory responses in colonic macrophages and epithelial cells in DSS-treated mice, Am J Physiol Gastrointest Liver Physiol, 2012, pp. G-504-G-514, vol. 302.
Zhang, et al., Evidence for the complementary and synergistic effects of the three-alkaloid combination regimen containing berberine, hypaconitine and skimmianine on the ulcerative colitis rats induced by trinitrobenzene-sulfonic acid, European Journal of Pharmacology, 2011, pp. 187-196, vol. 651.
Gofton, et al., Meloquine in the treatment of progressive multifocal leukoencephalopathy, J Neurol Psychiatry, 2011, pp. 452-455, vol. 82.
Kawashima, et al., Pharmacological Properties of Traditional Medicine (XXIX)1): Effect of Hange-shashin-to and the Combinations of Its Herbal Constituents on Rat Experimental Colitis, Biol. Pharm. Bull, 2004, pp. 1599-1603, vol. 27, No. 10.
ACT RX, To Save a Life, 2011, http://actrxlimited.com/content/products, 2 pages.
Yarnell, et al., Botanical Treatment and Prevention of Malaria, Alternative & Complementary Therapies, 2004, pp. 277-284, vol. 10, No. 6.
Wright, et al., Natural products and the development of selective antiprotozoal drugs, Phytotherapy Research, 1990, pp. 127-139, vol. 4, No. 4, 3pages, abstract.
Rosen, International Search Report for PCT/US12/61936, filed Oct. 25, 2012, mailed on Mar. 27, 2013, 17 pages.
Panda. 6 Artemisia Annua Cultivation, Herbs Cultivation and Medicinal Uses, National Institute of Industrial Re., 2000, 2nd Edition, 5 pages.
Nosten, et al., Artemisinin-Based Combination Treatment of Falciparum Malaria, Am. J. Trop. Med. Hyg., 2007, pp. 181-192, vol. 77.
Majori, Combined antimalarial therapy using artemisinin, Parassitologia, 2004, pp. 85-87, vol. 46, Nos. 1-2, 2 pages, abstract.
NutriCology, Innovation Nutrition, Leaders in Innovation and Purity, 2011-2012 Product Catalog, May 15, 2011, 116 pages.
Ferreira, et al., Flavonoids from Artemisia annua L. as Antioxidants and Their Potential Synergism with Artemisinin against Malaria and Cancer, Molecules, 2010, pp. 3135-3170, No. 15.
Rosen, et al., European Search Report for European Patent Application No. 12844536.8 filed May 12, 2014, dated Dec. 23, 2014, 8 pages.
Ansel, et al., Pharmaceutical Dosage Forms and Drug Delivery Systems, 1999, Seventh Edition, pp. 48, 50-53 and 89-91.
Kunimoto, et al., First case of (imported) babesiosis diagnosed in Canada, Can J Infect Dis, 1998, pp. 387-389, vol. 9, No. 6.
Centers for Disease Control and Prevention, Chikungunya Virus, retrieved Nov. 3, 2015, http://www.cdc.gov/chikungunya/, 3 pages.
WHO, Chikungunya, retrieved Nov. 3, 2015, http://www.who.int/mediacentre/factsheets/fs327/en/, 5 pages.

(56) References Cited

OTHER PUBLICATIONS

Akahata, et al., A virus-like particle vaccine for epidemic Chikungunya virus protects nonhuman primates against infection, Nature Medicine, 2012, http://www.nature.com/nm/journal/v16/n3/full/nm.2015.html, 4 pages.

National Institutes of Health / U.S. National Library of Medicine, MedlinePlus, Chikungunya virus, retrieved Nov. 3, 2015, https://www.nlm.nih.gov/medlineplus/ency/patientinstructions/000821.htm, 4 pages.

Shambuger, First human case of Chikungunya virus confiremed in Plano, The Dallas Morning News, Aug. 12, 2015, http://www.dallasasnews.com/news/community-news/plano/headlines/20150812-plano-announces-first-human-case-of-chikungunya-virus.ece, 4 pages.

More than 3000 cases of Chikungunya Virus in 16 states, Aug. 5, 2015, http://www.theyucatantimes.com/2012/08/more-than-3000-cases-of-chikungunya-virus-in-16-states/ 3 pages.

France-Presse, Spain detects first ever case of mosquito-borne chikungunya virus, Aug. 25, 2015, http://www.theguardian.com/world/2015/aug/26/spain-detects-first-ever-case-of-mosquito-bome-chikungunya-virus, 1 page.

Texas Department of State Health Services, Chikungunya Virus, retrieved Nov. 3, 2015, http://www.dshs.state.tx.us/idcu/disease/arboviral/chikv/, 1 page.

Harding, Mosquito virus fear hits Britons' Caribbean holidays: Tourists warned of deadly disease sweeping islands as thousands return home with agonising symptoms, Daily Mail, Nov. 14, 2014, http://www.dailymail.co.uk/travel_news/article-2834622/Britons-holidaying-Caribbean-warned-deadly-virus-sweeping-islands-37-retum-UK-suffering-agonising-symptoms.html, 11 pages.

Pan American Health Organization, World Health Organization, Chikungunya, retrieved on Nov. 4, 2015, http://www.paho.org/hq/?Itemid=40931, 1 page.

Chandak, et al., Neurological complications of Chikungunya virus infection, Neurological Society of India, 2009, pp. 177-180, vol. 57, issue 2, abstract.

Staples et al, Chikungunya Fever: An Epidemiological Review of a Re-Emerging Infectious Disease, Clinical Infectious Diseases, 2009, pp. 942-948, vol. 49, No. 6, abstract.

Cotter, First ever Chikungunya virus case pops up in York City, York Dispatch, Jun. 1, 2015, http://www.yorkdispatch.com/breaking/ci_28231567/first-ever-chikungunya-virus-case-pops-up-york, 2 pages.

Carpha's Interim Guidelines, Chikungunya Guidelines for Cruise Ships Coming to the Caribbean, Nov. 12, 2014, http://carpha.org/What-We-Do/Public-Health-Activities/Chikungunya, 3 pages.

Urquhart, What Scares Bug Experts, The horrible disease that experts feared would come to the United States has come to the United States, Jul. 2014, http://www.slate.com/articles/health_and_science/medical_examiner/2014/07/chikungunya_virus_in_the_united_states_cdc_and_other_experts_worried_about.htmal, 2 pages.

U.S. Phytotherapy, Inc., notification Concerning Transmittal of International Preliminary Report on Patentability, mailed May 8, 2014, 11 pages.

Komal, et al., Berberis Aristata: A Review, International Journal of Research in Ayurveda & Pharmacy, 2011, pp. 383-388, vol. 2, No. 2, 6 pages.

U.S. Phytotherapy, Inc., European Patent Application No. 12844536.8-1455, European Official Action mailed on Jan. 16, 2017, 8 pages.

\* cited by examiner

Figure 1

| | IC50 [dil. factor] | CC50 [dil. factor] |
|---|---|---|
| ZIKV | 4 | 1 |

# ALTERNATIVE ACT WITH NATURAL BOTANICAL ACTIVE GRAS INGREDIENTS FOR TREATMENT AND PREVENTION OF THE ZIKA VIRUS

RELATED APPLICATIONS

This invention claims the benefit of priority to U.S. Provisional Patent Application Ser. No. 62/306,973 filed Mar. 11, 2016, which in incorporated by reference in its entirety, and this application is also a Continuation-in-Part of U.S. patent application Ser. No. 14/933,229 filed Nov. 5, 2015, now allowed, which is a Continuation-in-Part of U.S. patent application Ser. No. 14/614,946 filed Feb. 5, 2015, now U.S. Pat. No. 9,186,331, which is a Divisional Patent Application of U.S. patent application Ser. No. 13/660,553 filed Oct. 25, 2012, now U.S. Pat. No. 9,011,892, which claims the benefit of priority to U.S. Provisional Patent Application Ser. No. 61/550,969 filed Oct. 25, 2011. The entire disclosure of each of the applications listed in this paragraph are incorporated herein by specific reference thereto.

FIELD OF INVENTION

This invention relates to novel therapeutic treatments and more specifically to compositions, methods and processes for preparing a novel Artemisinin Combination Therapy (ACT) that includes artemisinin, derivatives of artemisinin, berberine, capsaicin and *Tinospora Cordifolia* for prevention and treatment of Zika virus.

BACKGROUND AND PRIOR ART

About Zika Virus Disease

Zika virus was first discovered in 1947 and is named after the Zika forest in Uganda. In 1952, the first human cases of Zika were detected and since then, outbreaks of Zika were reported in tropical Africa, Southeast Asia, and the Pacific Islands. Zika outbreaks had probably occurred in many locations, but were undetected or unidentified. Before 2007, at least 14 cases of Zika had been documented, although other cases were likely to have occurred, likely to have been misdiagnosed and therefore were not reported.

Because the symptoms of Zika are similar to those of many other diseases, and until 2016 there was no known valid accurate clinical test for the virus, many cases may not have been recognized. It was first isolated from a rhesus monkey in the Zika forest, Uganda, in mosquitoes (*Aedes africanus*) in the same forest in 1948 and in humans in Nigeria in 1954. Zika virus is endemic in parts of Africa and Asia and was first identified in the South Pacific after an outbreak on Yap Island in the Federated States of Micronesia in 2007.

Zika virus is an emerging mosquito-borne virus first identified through a monitoring network of sylvatic yellow fever. It was subsequently identified in humans in 1952 first in Uganda and then the United Republic of Tanzania, then Nigeria. Outbreaks of Zika virus disease have now been recorded in Africa, North America and South America, Asia and the Pacific, and many Island Nations around the globe.

Zika virus is transmitted by the same type of mosquito that carries dengue fever, yellow fever, and chikungunya virus. A mosquito bites an infected person and then passes those viruses to other people it bites. Outbreaks did not occur outside of Africa until 2007, when it spread to the South Pacific.

The virus is of the Genre: Flavivirus; Vector: *Aedes* mosquitoes (which usually bite during the morning and late afternoon/evening hours) and Reservoir: Unknown.

Zika virus is a flavivirus, closely related to dengue. For almost 50 years, cases of Zika virus in humans had previously been reported in Africa, southern Asia and the Pacific Islands. Beginning in 2014, however, Zika virus outbreaks have occurred throughout the tropical and sub-tropical areas of the western hemisphere, as far north as Mexico and Puerto Rico. Now in 2016 cases have been officially reported as far north as Canada and the European continent. It is also known that Zika, dengue and chikungunya viruses are transmitted by mosquitoes mostly active during daytime, it's important that all travelers visiting affected areas continue to take protective measures to prevent mosquito bites throughout the day.

Zika virus infection is symptomatic in only about 1 out of every 5 cases. When symptomatic, Zika infection usually presents as an influenza-like syndrome, often mistaken for other arboviral infections like dengue or chikungunya. This necessitates the need for a treatment that will not harm patients who are misdiagnosed.

CDC Director Tom Frieden, MD, first told reporters that "on occasion," it may be spread through sexual contact or blood transfusions. In early February, 2016, a case of Zika spreading through sexual contact was reported in Dallas County, Tex. There, a person who'd traveled to an area that had cases of the virus infected a partner who had not traveled.

The CDC is aware of a report that Brazilian scientists have found the virus in the saliva and urine of infected people, Frieden said, but more definite information is needed.

Another similar mosquito, *Aedes albopictus*, also has the potential to transmit Zika virus, but has only been found in Australia, in the Torres Strait. These mosquito vectors typically breed in domestic water-holding containers; they are daytime biters and feed both indoors and outdoors near dwellings.

In French Polynesia, after a local Zika virus outbreak in 2013 and 2014, an increase in autoimmune and neurological diseases, such as, Guillain-Barré, had been observed. At this time, there is no proven link at this stage other than this temporal association. The simultaneous circulation of dengue serotype 1 and 3 viruses may also play a role.

Pathway of Virus in Mosquito

Infected blood travels to the midgut. Mosquito feeds on virus-infected blood. Virus enters the circulatory system. From there it travels to the salivary glands. Mosquito bites again, injecting virus-infected saliva into victim before feeding.

Only female mosquitoes bite people: they need blood in order to lay eggs. They pick up the virus in the blood. It travels from their gut through their circulatory system to their salivary glands and is injected into its next human victim. Mosquito saliva contain proteins that keeps blood from clotting. When a mosquito bites it first injects saliva so that its prey's blood does not clog its straw-like proboscis.

The Zika virus is also related to dengue, yellow fever and West Nile virus. After being discovered in the Zika forest in Uganda (1947) it remained confined to Africa and Asia and did not begin spreading widely in the Western Hemisphere until last May 2015, when an outbreak occurred in Brazil.

Until very recently (2015-2016), almost no one on the Western world had been infected. Few people here have any natural immune defenses against the virus, so it is spreading rapidly. Millions of people in tropical regions of the Americas may now have been infected.

Symptoms of the Zika Virus

The Zika virus disease is caused by the Zika virus that is spread to people primarily through the bite of an infected *Aedes* species mosquito. The most common symptoms of Zika are fever, rash, joint pain, and conjunctivitis (red eyes). The illness was originally thought to be mild with symptoms lasting for several days to a week after being bitten by an infected mosquito. People were thought not to be sick enough to go to the hospital, and few very rarely die of Zika. For these reasons, many people might not have realized that they had been infected. It was also believed that once a person has been infected, he or she is likely to be protected from future infections. It is now known that largely all of the above assumptions are incorrect.

The incubation period, the time from exposure to symptoms, of Zika virus disease is not exactly clear; there is not always a tell-tale mark or sign from the bite, but is likely to be a few days. The symptoms are similar to other arbovirus infections such as dengue, and include fever, skin rashes, conjunctivitis, muscle and joint pain, malaise, and headache. These symptoms are usually mild and last for 2-7 days.

During large outbreaks in French Polynesia and Brazil in 2013 and 2015 respectively, national health authorities reported potential neurological and auto-immune complications of Zika virus disease. Recently in Brazil, local health authorities have observed an increase in Guillain-Barré syndrome which coincided with Zika virus infections in the general public, as well as an increase in babies born with microcephaly in northeast Brazil. Agencies investigating the Zika outbreaks are finding an increasing body of evidence about the link between Zika virus and microcephaly. However, more investigation is needed to better understand the relationship between microcephaly in babies and the Zika virus. Other potential causes are also being investigated.

The disease can cause fever, rash, joint pain, and conjunctivitis, also called pinkeye. But most people won't know they have it. "Only about 1 in 5 people with the virus will exhibit symptoms," says Amesh Adalja, MD, a spokesman for the Infectious Diseases Society of America. "The vast majority have no symptoms at all." Adalja also says the virus rarely causes major complications. "It's never been thought of as a severe infectious disease until now."

In rare cases, Zika has been associated with Guillain-Barré syndrome, a disorder that can cause partial or complete paralysis, most often temporary but in some cases life-long. An increase in that illness has been seen in areas such as French Polynesia and Brazil, where a Zika epidemic has taken place, but research hasn't established a direct relationship between the two, according to the WHO's Regional Office for the Americas.

One case of Guillain-Barre that may be tied to Zika has been reported to the CDC, Frieden said. But "it's very challenging to make the link in an individual case," he said, as Guillain-Barre can also follow the flu or other infections.

Zika and other mosquito-borne illnesses, such as dengue fever, chikungunya, and West Nile virus cause a variety of flu-like symptoms that range in severity and can last from a few days to more than a week. As with Zika, some people infected with dengue or West Nile will not show any symptoms.

General Symptoms:

About 1 in 5 people infected with Zika virus become ill (i.e., develop Zika). The most common symptoms of Zika are fever, rash, joint pain, or conjunctivitis (red eyes). Other common symptoms include muscle pain and headache. The incubation period, the time from exposure to symptoms, for Zika virus disease is not known, but is likely to be a few days to a week.

The illness is usually mild with symptoms lasting for several days to a week after being bitten by an infected mosquito, however progression of the disease appears to be occuring with the greater numbers of those infected.

People usually don't get sick enough to go to the hospital, and they very rarely die of Zika. For this reason, many people might not realize they have been infected. Zika virus usually remains in the blood of an infected person for about a week but it can be found longer in some people.

Once a person has been infected, he or she is not likely to be protected from future infections.

Symptons also include, low-grade fever (between 37.8° C. and 38.5° C.), arthralgia, notably of small joints of hands and feet, with possible swollen joints. Myalgia, headache, retro-ocular headaches. Conjunctivitis, cutaneous maculo-papular rash, post-infection asthenia which seems to be frequent.

More rarely observed symptoms include digestive problems, such as, abdominal pain, diarrhea, constipation, mucous membrane ulcerations (aphthae), and pruritus.

Zika virus infection generally causes a non-severe disease with the possible exception of the effects to the fetus in pregnant women. Thus, pregnant women or women who may become pregnant are advised to take precautions. Immediately see a healthcare provider if you are pregnant and develop a fever, rash, joint pain, or red eyes within two weeks after traveling to a place where Zika has been reported. Be sure to tell the health care provider where you traveled.

As Zika infection may cause a rash that could be confused with other diseases such as measles or dengue, these more serious diseases need to be ruled out. Diagnosis of Zika infection will firstly be by exclusion, based on symptoms, travel history and exclusion of other diseases including measles and dengue.

Transmission

Specific areas with ongoing Zika virus transmission are often difficult to determine and are likely to change over time. Global climate changes are affecting the spread of the mosquito vectors and the virus is likely to be found in areas that have never had Aedes mosquitoes before. The CDC Travelers Health Site with the most updated travel information for those going to areas that are declared epidemic for Zika.

Diagnosis and Public Reporting

Zika virus infection should be considered in patients with acute onset of fever and polyarthralgia, especially travelers who recently returned from areas with known virus transmission.

The differential diagnosis of Zika virus infection varies based on place of residence, travel history, and exposures. Dengue and chikungunya viruses are transmitted by the same mosquitoes and have similar clinical features. The two viruses can circulate in the same area and can cause occasional co-infections in the same patient. Chikungunya virus infection is more likely to cause high fever, severe arthralgia, arthritis, rash, and lymphopenia, while dengue virus infection is more likely to cause neutropenia, thrombocytopenia, hemorrhage, shock, and death. It is important to rule out dengue virus infection because proper clinical management of dengue can improve outcome. In addition to dengue, other considerations include leptospirosis, malaria, rickettsia, group A streptococcus, rubella, measles, parvovirus, enteroviruses, adenovirus, other alphavirus infections (e.g., Mayaro, Ross River, Barmah Forest, O'nyong-nyong, and Sindbis viruses), post-infections arthritis, and rheumatologic conditions.

Preliminary diagnosis is based on the patient's clinical features, places and dates of travel, and activities. Laboratory diagnosis is generally accomplished by testing serum or plasma to detect virus, viral nucleic acid, or virus-specific immunoglobulin M and neutralizing antibodies.

Zika virus disease is a nationally notifiable condition. Healthcare providers are encouraged to report suspected Zika cases to their state or local health department to facilitate diagnosis and mitigate the risk of local transmission in many other countries and territories. Zika virus likely will continue to spread to new areas.

Global Concern

In May 2015, the Pan American Health Organization (PAHO) issued an alert regarding the first confirmed Zika virus infection in Brazil. On Feb. 1, 2016, the World Health Organization (WHO) declared Zika virus a Public Health Emergency of International Concern (PHEIC) regarding a recent cluster of microcephaly cases and other neurological disorders and the possible association of these illnesses with Zika virus infections. The WHO recommended efforts towards improved surveillance of and education regarding Zika virus as well as promotion of mosquito control. The WHO recommended no restrictions on travel or trade. Unfortunately, mosquito control has never been very effective, and given the sheer numbers of them and their longevity throughout the Earth's species; there is little chance of this option being worthwhile.

The WHO says Zika virus is "spreading explosively" in the Americas. Because it's been linked to birth defects in babies born to pregnant women, the CDC has issued travel warnings for pregnant women in countries where the disease has been found. Zika was thought to be primarily mosquito-borne, although now confirmed cases of sexual transmission have been reported.

As many as four million people could be infected by the end of the year. Officials at the Centers for Disease Control and Prevention have urged pregnant women against travel to about two dozen countries, mostly in the Caribbean and Latin America, where the outbreak is expanding exponentially. The infection appears to be linked to the development of unusually small heads and brain damage in newborns. Pregnant women who have been to these regions should be tested for the infection, the agency said.

Treatment

There are no specific treatments for Zika. There is no vaccine currently available. Zika is treated symptomatically, usually with bed rest, fluids, and medicines to relieve symptoms of fever and aching such as ibuprofen, naproxen, acetaminophen, or paracetamol. Aspirin should be avoided. Infected persons should be protected from further mosquito exposure during the first few days of the illness so they can not contribute to the transmission cycle.

As with the majority of mosquito-borne viral infections, there is no specific antiviral treatment for Zika virus however, it is important to exclude other, more serious infections for which there is targeted treatment or alternative clinical interventions available, including malaria and dengue virus, respectively.

Treatment of patients with Zika virus infection is entirely supportive, requiring rest, fluids, and pain and fever management. Individuals who have persistent joint pain may require additional supportive care including corticosteroids and/or physiotherapy.

Unfortunately, chloroquine is gaining ground as a possible treatment for the symptoms associated with Zika, and as an anti-inflammatory agent to combat the arthritis associated with Zika virus. A University of Malaya study found that for arthritis-like symptoms that are not relieved by aspirin and non-steroidal anti-inflammatory drugs (NSAID), chloroquine phosphate (250 mg/day) has given promising results. There is a debate about the appropriateness of chloroquine as treatment for Zika. Unpublished studies in cell culture and monkeys show no effect of chloroquine treatment on reduction of Zika disease.

Incorporated herein by reference is U.S. Pat. No. 9,011,892, Artemisinin with Berberine Compositions and Methods of Making, issued Apr. 21, 2015 to the present inventor; U.S. Pat. No. 9,011,892 demonstrated and listed ad nauseam, the ill side effects, psychological and physical dangers of using quinine and its many derivatives. Once again, primarily due to its low cost, remaining high stock counts, and the wrongful but familiar use for many years, we seem to be content to deal with a devil we know rather than expand our knowledge and build a better remedy.

Thus, there is need for a therapeutically effective treatment for humans and animals infected with the Zika virus disease. An antiviral treatment is provided by the Artemisinin Combination Therapy (ACT) of the present invention that includes artemisinin, derivatives of artemisinin, berberine, capsaicin and *Tinospora Cordifolia* for treatment of Zika virus.

SUMMARY OF THE INVENTION

A primary objective of this invention is to provide a composition of all-natural herbal ingredients for adults combining artemisinin, berberine, capsaicin and *Tinospora Cordifolia* formulated to deliver a therapeutically effective treatment for Zika virus disease.

A secondary objective of this invention is to provide a composition of all-natural herbal ingredients for children combining artemisinin, berberine, capsaicin and *Tinospora Cordifolia* formulated to deliver a therapeutically effective treatment for Zika virus disease.

A third objective of this invention is to provide a composition of all-natural herbal ingredients combining artemisinin, berberine, capsaicin and *Tinospora Cordifolia* for treatment and prevention of chloroquine-resistant strains of Zika virus in humans or animals.

A fourth objective of this invention is to provide a composition of all-natural herbal ingredients combining artemisinin, berberine, capsaicin and *Tinospora Cordifolia* that is devoid of quinine or quinine derivatives for treatment and prevention of Zika virus in humans or animals.

A fifth objective of this invention is to provide a composition of all-natural herbal ingredients combining artemisinin, berberine, capsaicin and *Tinospora Cordifolia* in a single pill, tablet or capsule, or delivery system that functions as a passively accurate dosing and delivery system for treatment and prevention of Zika virus in humans or animals.

A sixth objective of this invention is to provide a composition of all-natural herbal ingredients for children combining artemisinin, berberine, capsaicin and *Tinospora Cordifolia* in a chewable pill, tablet, or delivery system formulated to deliver a therapeutically effective treatment for Zika virus disease.

Further objects and advantages of this invention will be apparent from the figures and the following detailed description of a presently preferred embodiment, when read in conjunction with the appended claims.

BRIEF DESCRIPTION OF THE FIGURES

Figure 1:
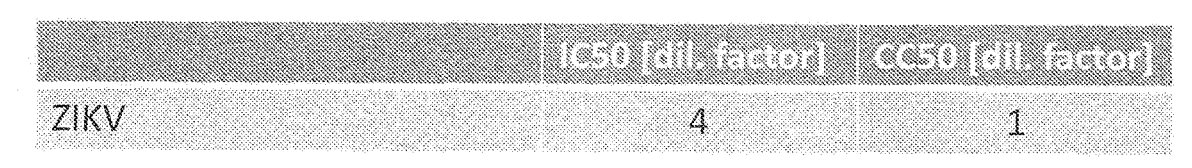

FIG. 1 is an overview of the efficacy of the composition of all-natural herbal ingredients, designated herein as PRO- ACT-ZIKA, in the treatment of the Zika virus, showing the inhibition concentration IC50 and the cytotoxic concentration CC50.

DETAILED DESCRIPTION OF THE PREFERRED EMBODIMENTS

Figure 2:
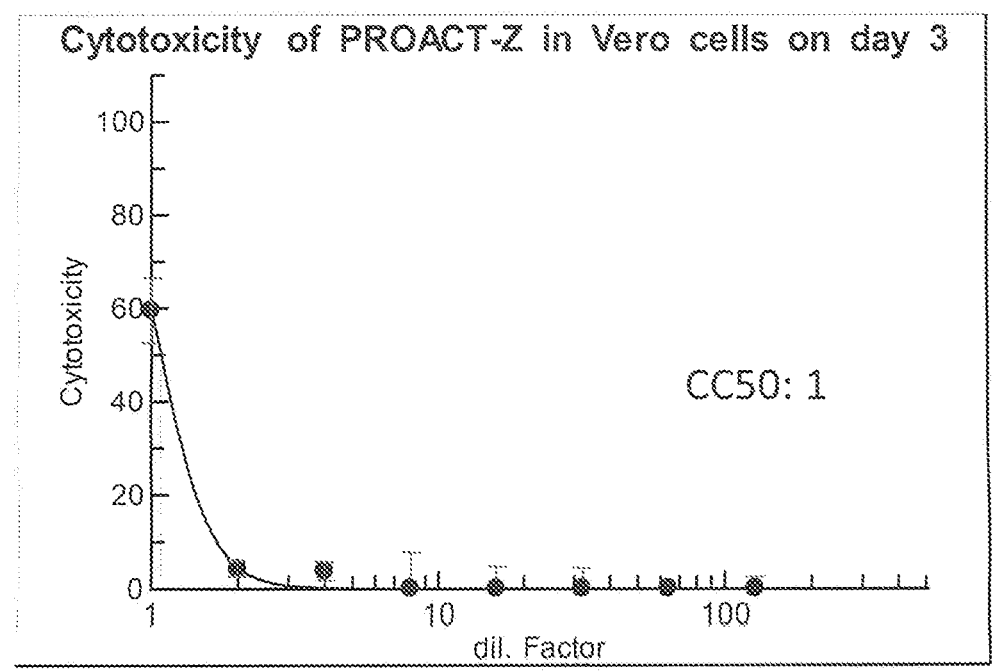
FIG. 2 is a graph of the cytotoxicity of the composition of all-natural herbal ingredients, PROACT-ZIKA, in Vero cells on day three.
Figure 3:
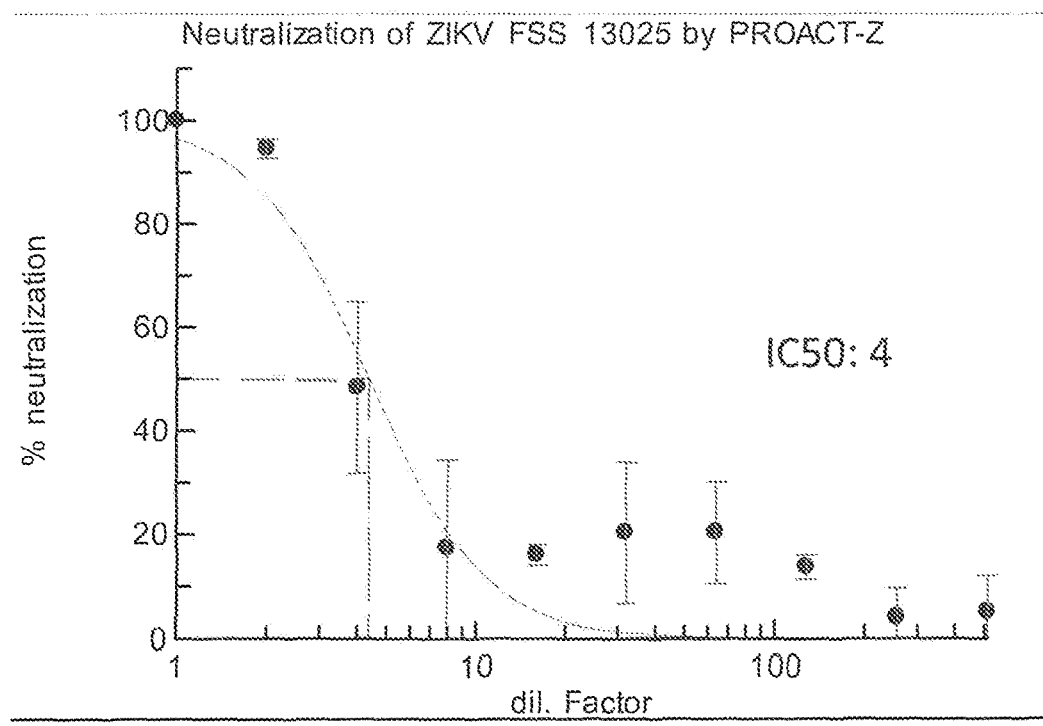
FIG. 3 is the graph of the neutralization of a specific Zika virus (KIKV FSS 13025) by the composition of all-natural herbal ingredients, PROACT-ZIKA.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

This invention claims the benefit of priority to U.S. Provisional Patent Application Ser. No. 62/306,973 filed Mar. 11, 2016, which in incorporated by reference in its' entirety, and this application is also a Continuation-in-Part of U.S. patent application Ser. No. 14/933,229 filed Nov. 05, 2015, now allowed, which is a Continuation-in-Part of U.S. patent application Ser. No. 14/614,946 filed Feb. 5, 2015, now U.S. Pat. No. 9,186,331, which is a Divisional Patent Application of U.S. patent application Ser. No. 13/660,553 filed Oct. 25, 2012, now U.S. Pat. No. 9,011,892, which claims the benefit of priority to U.S. Provisional Patent Application Ser. No. 61/550,969 filed Oct. 25, 2011. The entire disclosure of each of the applications listed in this paragraph are incorporated herein by specific reference thereto.

Incorporated herein by reference are the teachings in U.S. Pat. No. 9,011,892 regarding the method of formulating pills, capsules and therapeutic compositions of artemisinin and berberine for treatment of humans or animals. The present invention includes additional active ingredients that directly impact the Zika virus, these active ingredients include, but are not limited to, capsaicin and *Tinaspora Cordifolia*.

The delivery system described in this patent includes, but is not limited to, the following methods of packaging: blister packs, zip lock packs, standup pouches, foil pouches, boxes, jars, bottles, single dose packets, one a day packs, two day packs, three day packs, four day packs, five day packs, six day packs, seven day packs, 8, 9, 10 11, 12 or 13 or more day packs, fourteen day packs, 16, 16, 17, 18, 19, 20, 21, 22, 23, 24, 26, 26, 27, 28, 29 and thirty day packs or more, sixty day packs, ninety day packs, spray bottles, fast melt pill format, bursts, gel format adhesive bandages, skin patches, gelcaps, softgels, gelatin capsules, vegetarian capsules, hard shell gelatin capsules, injections, intravenous solutions, topical creams, topical ointments, suppositories, or sublingual methods of administration known to those versed in the art.

It would be useful to discuss the meanings of some words used herein and their applications before discussing the compositions of matter and method of preparing an alternative therapy with natural botanical active GRAS ingredients for treatment and prevention of the Zika virus.

The acronym ACT is used herein to mean "Artemisinin Combination Therapy" which includes artemisinin and its derivatives in combination with other therapeutic substances.

The acronym GRAS is used herein to mean "Generally Recognized as Safe" as a food ingredient by the U.S. Food and Drug Administration.

The acronym ZIKV is the testing laboratory designation for Zika virus.

The compound "crosmellose sodium" is an internally cross-linked sodium carboxymethylcellulose for use as a disintegrant in pharmaceutical formulations. The cross-linking reduces water solubility while still allowing the material to swell (like a sponge) and absorb many times its weight in water. As a result, it provides superior drug dissolution and disintegration characteristics, thus improving formulas' subsequent bioavailability by bringing the active ingredients into better contact with bodily fluids. Croscarmellose sodium also resolves formulators' concerns over long-term functional stability, reduced effectiveness at high tablet hardness levels, and similar problems associated with other products developed to enhance drug dissolution. Croscarmellose sodium is a very commonly used pharmaceutical additive approved by the U.S. Food and Drug Administration. Its purpose in most tablets—including dietary supplements—is to assist the tablet in disintegrating in the intestinal tract at the required location.

The term "excipient" is used herein to mean an inert substance added to a pharmaceutical composition to further facilitate administration of the compound. Excipients can include flavors, sugars, starches, cellulose derivatives, gelatin, calcium carbonate, magnesium stearate, silicon dioxide, masking agents and the like.

The term "preventative" and "prevent" is used herein to mean avoiding and preventing the appearance of clinical symptoms of a condition.

The term "therapeutically effective amount" is used herein to describe an amount of the composition being administered which will relieve to some extent or prevent one or more of the symptoms of the condition being treated.

The term "treating" and "treatment" is used herein to mean abrogating, substantially inhibiting, slowing or reversing the progression of a condition, substantially ameliorating clinical symptoms of a condition.

The present invention comprises all natural active ingredients formulated with various selected excipients to provide the treatments and therapies disclosed herein. This is an advantage over the prior art wherein chemicals and synthetic drugs are used for treatment and prevention. The use of chemicals can cause harmful side effects.

Before discussing the compositions of the present invention and the method for making, a brief discussion is provided of each of the all-natural active ingredients, artemisinin and berberine.

Artemisinin is produced from a plant-based source, the *Artemisia annua*. China and Vietnam provide 70% and East Africa 20% of the raw material. Seedlings are grown in nurseries and then transplanted into fields. It takes about 8 months to reach full size. The plants are harvested, the leaves are dried and sent to facilities where the artemisinin is extracted using solvent, typically hexane. Artemisinin and its derivative forms are commercially available from India or China. One supplier of artemisinin is Tai'an Zhonghui Plant Biochemical Co., Ltd. Taifeng Road, No. 88, Zhaizhen Industry District, Xintai, Shandong, China. Artemisinin and its derivatives have half-lives in the order of a few hours and thus require at least daily dosing for several days.

Berberine is a strongly yellow colored quaternary ammonium salt, known as an alkaloid. It is found in the roots, rhizomes, stems and bark of a variety of plants, including, but not limited to Barberry, Tree Turmeric, Goldenseal, Prickly Poppy, Californian Poppy and the like. In addition to use as a natural dye, berberine is considered an antibiotic and has been included in formulations as a traditional medicine or dietary supplement to treat fungal infections, *Candida albicans*, yeast, parasites, bacterial/viral infections, and eye infections with wide potential therapeutic properties.

Berberine is commercially available. One of many suppliers is Hopeland Chem-Tech Co., Ltd. Rm.2-0103, Gaoke Plaza D, No. 3, $4^{th}$ Gaoxin Road, Xi'an City, Shaanxi Province, China. Berberine is one of the bitterest substances known. It is also difficult to work within the formation of dry, physically stable pills due to its water content, which is approximately 14 weight %.

Capsaicin is an active component of chili peppers which are plants belonging to the genus *Capsicum*.

*Tinaspora Cordifolia* which is known by the common names Heart-leaved Moonseed, Guduchi and Giloy, is an herbaceous vine of the family Menispermaceae indigenous to the tropical areas of India, Myanmar and Sri Lanka. Its root, stems, and leaves are used in Ayurvedic medicine. *Tinospora cordifolia* is used for diabetes, high cholesterol, allergic rhinitis (hay fever), upset stomach, gout, lymphoma and other cancers, rheumatoid arthritis (RA), hepatitis, peptic ulcer disease (PUD), fever, gonorrhea, syphilis, and to boost the immune system.

Not to be bound by any theory, it is believed that artemisinin destroys the bacteria, virus or parasite in the blood and berberine destroys the weakened, but still viable bacteria, virus or parasite in the intestines. Capsaicin and *Tinospora cordifolia* support the action of artemisinin and berberine and function as a therapeutic combination having no known toxicity to humans at the dosage levels required for effective treatment and prevention of infections caused by the Zika virus in humans.

Table XA below provides a list of ingredients that are used to provide a preventative composition for an adult person in milligrams (mg) per pill, and the dosing required, for the treatment of Zika virus. Table XA is intended for treatment of an average adult weighing approximately 180 pounds (approximately 81.65 kg).

TABLE XA

Preventative Composition for Adults in mg per pill (2 capsules = 1 dosing configuration)

| Component-Preventative Adult Dosing | Broad Range (mg per Pill) | Preferred Range (mg per Pill) | Preferred Amt (mg per Pill) | Substitution Category |
|---|---|---|---|---|
| ACTIVE INGREDIENTS | | | | |
| Artemisinin | 25-60 mg | 45-55 mg | approx 50 mg | |
| Berberine | 175-500 mg | 300-450 mg | approx 400 mg | |
| Capsaicin | 150-300 mg | 200-275 mg | approx 225 mg | |
| *Tinaspora Cordifolia* | 80-175 mg | 100-150 mg | approx 125 mg | |
| BLENDED MIXTURE* | 0-500 mg | 300-500 mg | approx 350 mg | Excipient with Active ingredients |
| INERT INGREDIENTS | | For binding or delivery of other ingredients. | | |
| microcrystalline cellulose | 0-650 | 400-650 | approx 540 | Binders and compaction |
| stearic acid | 0-200 | 200-400 | approx 300 | Lubricant excipient |
| silicon dioxide | 0-50 | 30-50 | approx 40 | Water reducing agent and to promote absorption of water and prevent caking and clumping |
| calcium carbonate | 0-1100 | 800-1100 | approx 1000 | Inert filler |
| magnesium stearate | 0-90 | 60-90 | approx 75 | For lubricating properties and to prevent powdered component from sticking to pill press equipment during the compression from powder into solid tablets |
| croscarmellose sodium | 0-50 | 35-50 | approx 40 | To reduce water solubility and allow material to expand, absorbing many times its weight in water and removing much of the water from berberine. |

*The blended mixture and inert ingredients are used only when making a compressed pill.

Approximately, herein abbreviated as "approx," is defined as +/−5% in order to cover manufacturing variances and dosing tolerances.

In the tables, a gel cap example can consist of only artemisinin, berberine, capsaicin, and *Tinospora cordifolia* in amounts referenced in the above tables.

The inert ingredients are not therapeutic and are designed for the integrity, palatability and stability of the tablets. There are many substitutes for the various classes of inert ingredients that can include disintegrants, lubricants, binders, and excipients.

Disintegrants can include, but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating agents or desiccating agents can include but are not limited to sodium carboxy methyl cellulose, silica gel, microcrystalline cellulose, carboxymethylcellulose calcium, cellulose, colloidal silicone dioxide, and crosscarmellose sodium.

The blended mixture referenced in Table XA can include a blended mixture approximately 400 mg of concentrate of black walnut (*Juglans nigra*) dry outer hull; approximately 500 mg of concentrate of organically grown wormwood (*Artemisia absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

For adults, defined as persons with a body weight of at least 110 pounds, two capsules per day with a meal is taken for 7 to 14 days depending on the number of days desired to Two capsules per day for 7 to 14 days is effective for preventing infection for 30 to 60 days, respectively.

Table XB below covers a dose per body weight (in mg per kg) for customizing dosages for adults less than or greater than 180 pounds (81.65 kgs), for the treatment of Zika virus.

TABLE XB

| DOSE PER BODY WEIGHT FOR ADULTS (mg per kg) | | | | |
|---|---|---|---|---|
| Component Preventative-Adult Dosing | Broad Range (mg per kg) | Preferred Range (mg per kg) | Preferred Amt ((mg per kg) | Substitution Category |
| ACTIVE INGREDIENTS | | | | |
| Artemisinin | 22.68-54.43 | 40.82-49.89 | approx 45.36 | |
| Berberine | 158.76-453.60 | 272.15-408.03 | approx 362.87 | |
| Capsaicin | 68.18-136.36 | 90.91-125.00 | approx 102.27 | |
| *Tinaspora Cordifolia* | 36.36-79.55 | 45.45-68.18 | approx 136.36 | |
| BLENDED MIXTURE* | 0-226.80 | 136.08-226.80 | approx 158.76 | Excipient with Active ingredients |
| INERT INGREDIENTS | | For binding or delivery of other ingredients. | | |
| microcrystalline cellulose | 0-294.83 | 181.94-294.83 | approx 244.94 | Binders and compaction |
| stearic acid | 0-181.44 | 90.72-181.44 | approx 136.08 | Lubricant excipient |
| silicon dioxide | 0-22.68 | 13.61-22.68 | approx 18.14 | Water reducing agent and to promote absorption of water and prevent caking and clumping |
| calcium carbonate | 0-498.95 | 362.89-498.95 | approx 453.59 | Inert filler |
| magnesium stearate | 0-40.82 | 27.22-40.82 | approx 34.02 | For lubricating properties and to prevent powdered component from sticking to the pill press equipment during the compression from powder into solid tablets |
| croscarmellose sodium | 0-22.68 | 15.88-22.68 | approx 18.14 | To reduce water solubility and allow the material to expand, absorbing many times its weight in water and removing much of the water from Berberine. |

*The blended mixture and inert ingredients are used only when making a compressed pill.

Approximately is defined as +/−5% in order to cover manufacturing variances and dosing tolerances.

In the tables, a gel cap example can consist of only artemisinin, berberine, capsaicin, and *Tinospora Cordifolia* in the amounts referenced in the above tables.

The blend mixture referenced in Table XB can consist of a blended mixture approximately 400 mg of concentrate of black walnut (*Juglans nigra*) dry outer hull; approximately 500 mg of concentrate of organically grown wormwood (*Artemisia absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

The inert ingredients are not therapeutic and are designed for the integrity, palatability and stability of the tablets. There are many substitutes for the various classes of inert ingredients. The following classes of inert ingredients can include, but are not limited to, disintegrants, lubricants, binders, and excipients.

Disintegrants can include but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating agents or desiccating agents can include but are not limited to sodium carboxy methyl cellulose, silica gel, microcrystalline cellulose, carboxymethylcellulose calcium, cellulose, colloidal silicone dioxide, and crosscarmellose Sodium.

Approximately is defined as +/−5% in order to cover manufacturing variances and dosing tolerances.

In the tables, a gel cap example can consist of only artemisinin, berberine, capsaicin, and *Tinospora Cordifolia* in the amounts referenced in the above tables.

Thus, someone skilled in the art makes a judicious selection of an appropriate dosage regimen; selection is dependent on the age or body weight of the patient, condition to be treated and the judicious selection is not a limitation of the present invention.

Methods of Manufacturing Tablets, Pills and Capsules

Our product by design and claim states a "passively accurate dosing system." Our manufacturing claims stated herein make it extremely possible to maintain and honor those claims. However, one can never preclude the possibility of the existence of some variance when mixing powdered compounds under high pressure. Although the FDA stated in a 2004 letter from Dr. Steven Galson, then director of the Center for Drug Evaluation and Research at the FDA and now U.S. Surgeon General, that −20/+25%, "actually represents the acceptable bounds on the 90% confidence intervals around the ratio of the mean result for products." Therefore, the FDA accepts those high deviations as normal, our concern was for tolerances at those extreme limits. However, while we believe there to be a reasonable amount of efficacy and safety at these extremes; we do not expect to exceed plus or minus 5% of our stated ingredient values.

Before the two active ingredient raw materials are accepted by the manufacturing laboratory, a chemical analysis of the composition is performed by an independent, third party commercial laboratory. This analysis confirms the purity of the materials as well as other compounds that might be present in the shipment. Industry standards for purity and other compounds are known and used to accept or reject a shipment.

Once the product is manufactured but before it is packaged, random batch samples are sent to another independent, third party commercial analysis laboratory where the pills are inspected and broken down to determine their content. The dosing amounts are maintained as stated on the packaging, and the pills must be free of any contaminants. Failure to obtain the analysis laboratory approval results in a rejection of the batch.

In the Examples below, two types of compounds previously identified as anti-malarial agents and two active botanicals for pain relief are combined into one single pill. Artemisinin is a plant-based terpenoid compound that is known for use as an anti-malarial agent. Berberine is a plant-based alkaloid with a very bitter taste and water content in a range of approximately 14 wt. %. Capsaicin is an active component of chili peppers that causes an endorphin rush that makes capsaicin an effective remedy for pain and other medical conditions. *Tinaspora Cordifolia* is used to boost the immune system. Successful bonding and adhesion through use of non-active ingredients is essential in order to produce a compressed, physically stable pill. Adding granulation steps to the process reduces water and subsequently reduces the amount of non-active ingredients or excipients needed.

In addition, the manufacturing process solves the problem of keeping the formulated pill from becoming hydrated during shipment and storage in tropical climates by using blister packing immediately at the end of processing to maintain chemical composition and stability.

Evaluation of Product

An independent testing laboratory, IBT BioServices, Gaithersburg, Md. 20878, provided results of a study, BS-2082, the laboratory study control number, covering PROACT-ZIKA, the tradename for the product of the present invention. PROACT-ZIKA is designed to work as a therapeutic agent against the Zika virus, ZIKV is the laboratory shorthand for the Zika virus, and a Plaque reduction neutralization assay test is used to quantify the titre of neutralizing antibody for a virus.

Statement of Work

First, PROACT-ZIKA was tested in a plaque-reduction neutralization (PRN) assay against ZIKV FSS 13025 (a recognized certain strain of Zika (a flavivirus, which is a genus of viruses in the family Flaviviridae). Subsequently, cytotoxicity was determined in Vero cells (host cells for growing a virus in vitro) at day 3 after a 1-hour contact time on the cells.

Methodology for Measuring Neutralization

One method in the Plaque reduction neutralization test (PRN), Virus stock was diluted to ~250 PFU (Plaque Forming Units) in serum-free medium. PROACT-ZIKA was prepared fresh at the day of study. Ten (10) 2-fold serial dilutions were prepared for the plaque-reduction neutralization assay.

In a second method, the virus and PROACT-Z dilutions were mixed 1:1 and incubated for 2 hours at 37° C. Vero cells (host cells for growing viruses) seeded in 24-well plates were infected with the dilutions for one hour.

Then 0.8% methylcellulose was added to each well. Methyl cellulose is used in cell culture to study viral replication. It is dissolved in the same nutrient-containing medium in which cells are normally grown. A single layer of cells are grown on a flat surface, then infected with a virus for a short time. The strength of the viral sample used will determine how many cells get infected during this time.

Cells were fixed after 3 days and analyzed in a plaque assay. Plates were scanned and the plaque counts were used to calculate the PRNT50 using a 4PL curve fit (Four parameter model for ELISA assay analysis). The PRNT50 value is the concentration of serum necessary to reduce the number of plaques by 50% compared to the serum free virus, which gives the measure of how effective it is. ELISA is a test that detects and measures antibodies in the blood of humans or animals.

Methodology for Measuring Cycotoxicity

PROACT-Z was prepared as stated for the PRNT assay. Seven (7) 2-fold serial dilutions were prepared for the cytotoxicity assay. PROACT-Z dilutions were mixed 1:1 with medium and incubated for 2 h at 37° C.

Then, Vero cells seeded in 96-well plates were incubated with the dilutions for 1 hour. Cytotoxicity was evaluated on day 3 using Promega's CellTiter-Glo kit (A bioluminescence based cell viability assay to detect living cells in a culture based on quantitation of the Adenosine triphosphate (ATP), which transports chemical energy within cells for metabolism, which indicates the presence of metabolically active cells.

FIG. 1 shows that PROACT-ZIKA used in a dilution factor of 4 is required to kill 50% of the Zika virus (ZIKV) in vitro; and PROACT-ZIKA in a dilution factor of 1 is the cytotoxic concentration to cause death to 50% of viable cells in the virus infected host cells. In other words, IC50 is how much of PROACT-ZIKA, is necessary to inhibit viral growth by half. CC50 is how much of PROACT-ZIKA, is necessary to be toxic to one half of the infected host cells.

FIG. 2 shows cytotoxicity of PROACT-ZIKA in Vero cells, the host cells for growing the virus, on day three. The PROACT-ZIKA with a dilution factor of 1 causes the death of 50% of viable cells in the virus infected host cells.

FIG. 3 shows the percentage of neutralization of a Zika virus (ZIK FSS 13025) by PROACT-ZIKA over a range of dilution factors from zero to more than 100. The PROACT-ZIKA with a dilution factor of 4 inhibits 50% of the Zika virus growth.

In summary, the present invention solves the problem of preventing the spread of the mosquito-borne Zika virus disease. Prior to this invention, there is no known treatment or pill specifically formulated to treat and prevent the Zika virus disease. In addition to therapeutic benefits, the present invention solves the problem of incorrect dosages by self-administering patients, inaccurate combining of ACTs which leads to non-therapeutic results, and a chewable form of tablet or pill agreeable to children.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A composition of all all-natural herbal ingredients formulated for treatment of humans and animals exposed to Zika virus, comprising active botanical ingredients, in combination:

artemisinin and derivatives thereof;
berberine;
capsaicin; and
*Tinospora Cordifolia*, wherein the combination of active botanical ingredients,
the artemisinin and derivatives thereof;
the berberine;
the capsaicin; and
the *Tinospora Cordifolia*, are packaged in at least one of: a single pill, tablet, capsule, gelcap, oral suspension, sublingual or transdermal patch, and wherein the composition is useful for killing Zika virus disease.

2. The composition of claim 1, wherein the composition for human adults includes approximately 25 to approximately 60 milligrams (mg) artemisinin;
approximately 175 to approximately 500 milligrams (mg) berberine;
approximately 150 to approximately 300 millligrams (mg) capsaicin; and
approximately 80 to approximately 175 milligrams (mg) *Tinospora Cordifolia*.

3. The composition of claim 2, wherein the composition for human adults includes approximately 45 to approximately 55 milligrams (mg) artemisinin;
approximately 300 to 450 milligrams (mg) berberine;
approximately 200 to approximately 275 millligrams (mg) capsaicin; and
approximately 100 to approximately 150 milligrams (mg) *Tinospora Cordifolia*.

4. The composition of claim 3, wherein the composition for human adults includes approximately 50 milligrams (mg) artemisinin;
approximately 400 milligrams (mg) berberine;
approximately 225 millligrams (mg) capsaicin; and
approximately 125 milligrams (mg) *Tinospora Cordifolia*.

5. The composition of claim 1, wherein the composition includes at least one inert binding or delivery component selected from the group comprising: microcrystalline cellulose, stearic acid, silicon dioxide, calcium carbonate, magnesium stearate and croscarmellose sodium used when forming a compressed pill.

6. A composition of active botanical ingredients for treating an adult patient in a single pill, tablet or capsule comprising, in combination:

artemisinin and derivatives thereof;
berberine;
capsaicin;
*Tinospora Cordifolia*; and
a blended mixture of up to approximately 400 mg of concentrate of black walnut dry outer hull; approximately 500 mg of concentrate of organically grown wormwood dry flower and leaf; approximately 150 mg of concentrate of Clove dry flower; and approximately 700 mg of fresh leaf organically grown Chinese wormwood, wherein the composition is useful for killing Zika virus.

7. The composition of claim 6, wherein the composition for human adults includes
approximately 25 to approximately 60 milligrams (mg) artemisinin;
approximately 175 to approximately 500 milligrams (mg) berberine;
approximately 150 to approximately 300 millligrams (mg) capsaicin; and
approximately 80 to approximately 175 milligrams (mg) *Tinospora Cordifolia*.

8. The composition of claim 7, wherein the composition for human adults includes
approximately 45 to approximately 55 milligrams (mg) artemisinin;
approximately 300 to 450 milligrams (mg) berberine;
approximately 200 to approximately 275 millligrams (mg) capsaicin; and
approximately 100 to approximately 150 milligrams (mg) *Tinospora Cordifolia*.

9. The composition of claim 8, wherein the composition for human adults includes
approximately 50 milligrams (mg) artemisinin;
approximately 400 milligrams (mg) berberine;
approximately 225 millligrams (mg) capsaicin; and
approximately 125 milligrams (mg) *Tinospora Cordifolia*.

10. A method for making the composition of claim 1 for an adult patient in a single pill, tablet, capsule, gelcap, oral suspension, sublingual or transdermal patch, or any other therapeutic preparation comprising the steps of:
   a) providing a mixer;
   ai) selecting an amount of artemisinin from a range of approximately 25 mg to approximately 60 mg;
   aii) selecting an amount of berberine from a range of approximately 175 mg to approximately 500 mg;
   aiii) selecting an amount of capsaicin from a range of approximately 150 mg to approximately 300 mg;
   aiv) selecting an amount of *Tinospora Cordifolia* from a range of approximately 80 mg to approximately 175 mg;
   b) mixing artemisinin, berberine, capsaicin, and *Tinospora Cordifolia* in the mixer to form mixture (I);
   c) mixing at least one binding or delivery component with mixture (I) to form mixture (II);
   d) filtering mixture (II) through at least one filter to form mixture (III);
   e) placing mixture (III) in a granulator;
   f) granulating mixture (III) in the granulator to produce granulated chips;
   g) pressing the granulated chips into tablets (Mixture IV);
   h) removing dust from the tablets by cleaning and vacuuming the tablets;
   i) applying an enteric shell coating to the cleaned and vacuumed tablets;
   j) heating and tumbling the coated tablets; and
   k) packaging the heated and tumbled coated tablets in a package.

11. The method for making the composition in claim 10, wherein the mixing step (b) further includes the steps of:
selecting approximately 25 to approximately 60 milligrams (mg) artemisinin;
selecting approximately 175 to approximately 500 milligrams (mg) berberine;
selecting approximately 150 to approximately 300 millligrams (mg) capsaicin; and
selecting approximately 80 to approximately 175 milligrams (mg) *Tinospora Cordifolia*.

12. The method for making the composition in claim 11, wherein the mixing step (b) further includes the steps of:
selecting approximately 45 to approximately 55 milligrams (mg) artemisinin;
selecting approximately 300 to approximately 450 milligrams (mg) berberine;
selecting approximately 200 to approximately 275 millligrams (mg) capsaicin; and
selecting approximately 100 to approximately 150 milligrams (mg) *Tinospora Cordifolia*.

13. The method for making the composition in claim 12, wherein the mixing step (b) further includes the steps of:
selecting approximately 25 to approximately 60 milligrams (mg) artemisinin;
selecting approximately 175 to approximately 500 milligrams (mg) berberine;
selecting approximately 150 to approximately 300 millligrams (mg) capsaicin; and
selecting approximately 80 to approximately 175 milligrams (mg) *Tinospora Cordifolia*.

14. The method for making the composition in claim 12, wherein the mixing step (b) further includes the steps of:
selecting approximately 50 milligrams (mg) artemisinin;
selecting approximately 400 milligrams (mg) berberine;
selecting approximately 225 millligrams (mg) capsaicin; and
selecting approximately 125 milligrams (mg) *Tinospora Cordifolia*.

15. The method for making the composition in claim 10, wherein the mixing step includes the step of:
selecting at least one binding or delivery component from the group comprising: microcrystalline cellulose, stearic acid, silicon dioxide, calcium carbonate, magnesium stearate and croscarmellose sodium.

* * * * *